United States Patent [19]

Benjamin et al.

[11] Patent Number: 5,254,276
[45] Date of Patent: * Oct. 19, 1993

[54] DIOL PHOSPHITE ADDUCTS OF OLEFINS AS MULTIFUNCTIONAL LUBRICANTS AND ADDITIVES FOR LUBRICANTS

[75] Inventors: Linda A. Benjamin, Westville; Andrew G. Horodysky, Cherry Hill, both of N.J.; Derek A. Law, Yardley; Shi-Ming Wu, Newtown, both of Pa.

[73] Assignee: Mobil Oil Corporation, Fairfax, Va.

[*] Notice: The portion of the term of this patent subsequent to Dec. 10, 2008 has been disclaimed.

[21] Appl. No.: 829,653

[22] Filed: Feb. 3, 1992

Related U.S. Application Data

[63] Continuation-in-part of Ser. No. 641,326, Jan. 15, 1991, abandoned, which is a continuation of Ser. No. 292,066, Dec. 30, 1988, abandoned.

[51] Int. Cl.$^5$ .................. C10M 137/12; C07F 9/02
[52] U.S. Cl. .................. 252/49.8; 558/77; 558/83
[58] Field of Search .............. 558/77, 83; 252/49.8

[56] References Cited

U.S. PATENT DOCUMENTS

| | | | |
|---|---|---|---|
| 2,411,762 | 11/1946 | Swern | 260/348 |
| 2,455,892 | 12/1948 | Fraser | 252/41 |
| 2,457,329 | 12/1948 | Swern et al. | 260/348 |
| 2,957,931 | 10/1960 | Hamilton et al. | 260/403 |
| 3,341,547 | 9/1967 | Mailey | 260/302 |
| 3,632,510 | 1/1972 | LeSuer | 252/35 |
| 3,632,511 | 1/1972 | Liao | 252/51.5 |
| 3,697,428 | 10/1972 | Meinhardt et al. | 252/56 |
| 3,725,441 | 4/1973 | Murphy | 260/400 |
| 3,795,612 | 3/1974 | Stournas et al. | 252/46.6 |
| 4,093,588 | 6/1978 | Spivack et al. | 260/45.8 R |
| 4,532,057 | 7/1985 | Horodysky et al. | 252/49.8 |
| 4,704,218 | 11/1987 | Horodysky et al. | 252/46.6 |
| 4,776,969 | 10/1988 | Ryer et al. | 252/46.7 |
| 5,071,577 | 12/1991 | Benjamin et al. | 252/46.6 |
| 5,104,579 | 4/1992 | Benjamin et al. | 252/46.6 |

Primary Examiner—Jerry D. Johnson
Attorney, Agent, or Firm—Alexander J. McKillop; Malcolm D. Keen; Howard M. Flournoy

[57] ABSTRACT

Cyclic diol- and diol-ester phosphite adducts of olefins and polymeric olefins provide superior multifunctional and lubricating fluid media with internal synergistic multifunctional antiwear, antioxidant properties and extreme pressure/antiwear additives for both mineral and synthetic lubricating oils as well as liquid hydrocarbon fuels.

19 Claims, No Drawings

DIOL PHOSPHITE ADDUCTS OF OLEFINS AS MULTIFUNCTIONAL LUBRICANTS AND ADDITIVES FOR LUBRICANTS

CROSS-REFERENCE TO RELATED CASES

This case is a continuation-in-part of application Ser. No. 07/641,326, filed Jan. 15, 1991, now abandoned, which is a continuation of Ser. No. 07/292,066, filed Dec. 30, 1988, now abandoned.

BACKGROUND OF THE INVENTION

This invention is directed to superior multifunctional lubricating media with internal synergistic multifunctional properties and to the use of minor amounts of such media as multifunctional additives in lubricating oils and liquid hydrocarbon fuels. More particularly this application is directed to lubricant oils and greases prepared therefrom and hydrocarbon fuels having multifunctional amounts, cyclic diol- and diol-ester phosphite adducts of olefins and polymeric olefins.

The general peroxide catalyzed reaction of dialkyl hydrogen phosphites with conventional olefins to give phosphonate derivatives is known as disclosed in U.S. Pat. No. 2,957,931. The use of these materials as multifunctional additives in a variety of lubricant applications is also known. These products have demonstrated excellent high and low temperature lubricating properties with exceptional EP/antiwear properties with potential friction reducing and corrosion inhibiting properties.

The use of ester-containing or polymeric ester type carboxylic materials as commercial lubricant and fuel additives are well known and are described in such U.S. Pat. Nos. as 3,341,547, 3,632,510, 3,632,511, 3,697,428, or 3,725,441 these have been used in a variety of commercial lubricant and fuel applications for decades.

The use of sulfur-ester containing additives have been reported in literature primarily in polymer stabilizing application, however, no prior art known to applicants discloses and/or claims lubricant compositions or fuel compositions comprising reaction products of polymeric olefins with diol- and/or diol-type ester derived phosphites, or the use of such products themselves as the base lubricant. Additionally, no art known to applicants is believed to teach or suggest the present invention.

SUMMARY OF THE INVENTION

It has now been found that functionalized compositions in accordance with this invention may be used as lubrication oils and greases and in liquid hydrocarbon fluid compositions, and in minor amounts as additives in fuels or in synthetic or mineral oils of lubricating viscosity or greases prepared therefrom. Accordingly, cyclic and oligomeric diol- and diol-ester phosphite derived adducts of olefins and polymeric olefins provide unique multifunctional additives as well as multifunctional lubricant and fuel compositions with inherent multifaceted internal synergism.

The coupling of olefinic materials with the non-traditional multifunctional phosphite derivatives described in this application leads to novel lubricants and lubricant or fuel additives with increased or enhanced oxidative stability, reduced wear, and improved rust inhibition and increased load carrying capabilities. In addition, since the phosphite moiety is grafted onto the olefin backbone undesirable properties such as volatility and staining are eliminated.

The remarkable benefits of this invention are also expected for a variety of synthetic and mineral oil base lubricant basestocks and greases and for hydrocarbon, alcoholic or hydrocarbon and alcoholic fuels intended for use in internal combustion engines or for heating applications. Both the compositions of matter and the lubricant and fuel compositions containing same are believed to be novel. To the best of our knowledge these compositions have not been previously disclosed or used in lubricating oils, greases, or fuel applications.

DETAILED DESCRIPTION OF THE SPECIFIC EMBODIMENTS

The additive products described herein are generally made by reacting olefinic materials selected from the group consisting of $C_2$ to about $C_{80}$ hydrocarbyl alpha or internal olefins, oligomers or polymers thereof, olefinic esters and olefinic ethers having at least one free olefinic group with a functionalized cyclic or oligomeric diol derived phosphite or diol-ester derived phosphite wherein said functionalized reactant is selected from the group consisting of an aliphatic vicinal diol derived phosphite, sulfide-containing vicinal diol derived phosphites, ether-alcohol derived phosphites, amino-alcohol derived phosphites and aromatic derived phosphites or hydrogen phosphites.

The incorporation of the functionalized phosphite derivatives onto the backbone of olefinic polymeric oils provides the basis for the unique internal synergistic extreme pressure/antiwear activity, thermal stability and lubricity. Functionalized phosphite-adducts will also contribute additional friction reducing, rust inhibiting and hydrolytic stabilizing benefits. All of the above-mentioned properties are believed to be enhanced as a result of the novel multidimensional internal synergism of the composition of matter and lube and fuel compositions in accordance with this invention.

The use of these functionalized compositions, as detailed in this application, as lubrication fluids and additives in either a mineral or synthetic lubricant is unique and provides unprecedented performance benefits due to this inherent internal synergism. For example, the process of improving wear, friction, corrosion inhibition and thermal stability of a polymeric polyisobutylene lubricating oil via the addition of 0-100% of an adduct of a cyclic or oligomeric diol-derived phosphite and a polymeric polyolefin, i.e., polyisobutene, polyoctene and/or polydecene derived lubricating oil is unique and not reported in prior art. Incorporation of functionalized phosphites onto the backbone of the olefin-containing polymeric oils offers unique advantages over conventional formulated lubricants where volatility or extraction is considered to be important. The products from novel functionalized phosphites with polymeric oils are unique and not evident in prior art.

Any post-reactions of these unique functionalized phosphite olefins with small amounts of functionalized olefins such as vinyl esters, vinyl ethers, acrylates and methacrylates are also believed to be novel. For example, polyisobutylene adducts of aliphatic vicinal diol derived phosphites (I) should possess antiwear properties and are expected to exhibit friction reduction and enhanced hydrolytic stability and additive solubilizing features from the vicinal diol group. Analogous sulfide-containing vicinal diol derived phosphite (II) lube olefin adducts provide better antioxidant/antiwear properties.

These effects are synergistic due to both sulfur and phosphorus incorporation. Similarly, ether alcohol derived phosphite (III) adducts of olefins and polyisobutylene provide improved chelating ability and solubility/detergency with the ether linkage. Amino-alcohol derived phosphite (IV) adducts improve rust inhibition and emulsibility/demulsibility properties. Hydroxyester derived phosphite adducts (V) improve frictional properties, rust inhibiting characteristics and additive solubility in highly paraffinic base fluids. Aromatic derived phosphites, e.g., catechol, (VI) resorcinol, phenolic or substituted catechol, resorcinol, phenolic, all contain an intrinsic synergistically placed antioxidant group which may be released under hydrolytic conditions or otherwise in service conditions. In addition, these multifaceted phosphite adducts exhibit antiwear properties and friction modifying properties.

All of the above mentioned olefin-phosphite adducts exhibit beneficial properties from the unique olefin in combination with those properties unique to a given functionalized phosphite, and this combination provides for a novel structural class and a unique multifaceted synergistic set of properties.

The selected multifunctional phosphorus-containing moieties referred to hereinabove:

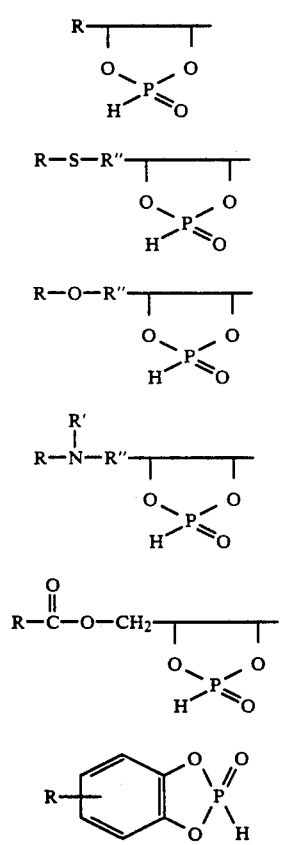

open chain phosphites of (I) can be exemplified by

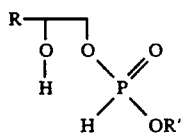

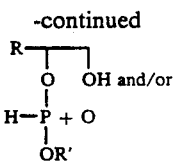

where R is an alkyl group of 1 to 12 carbon atoms, phenyl, phenyl substituted by alkyl of 1 to 18 carbon atoms, aralkyl and substituted aralkyl derivatives and can optionally contain oxygen, sulfur and/or nitrogen, and where R' is hydrogen or a $C_1$ to $C_{30}$ such as dimethyl or dibutyl phosphite hydrocarbyl group in general, and R" equals $C_2$ to $C_{30}$ hydrocarbyl and can additionally contain S, N, O moieties or mixtures thereof.

The phosphite can also be chosen from one of the multifunctional derivatives illustrated above. Appropriate phosphites also includes non-cyclic, open chain phosphites of each of the appropriate diols and/or ester-derived diols.

Finally, more traditional type phosphite adducts will also provide a final product with improved antiwear, and possibly friction reducing properties. For example, reaction products of polyisobutylene or similar olefin, with a hydrogen phosphite of the following formula.

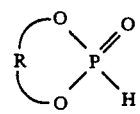

Suitable phosphates can also include

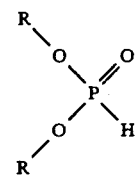

R is as defined above, such as dimethyl or dibutyl phosphite.

The polymeric olefin can be from about 200 to 20,000 molecular weight units. Other useful olefins can also include lower molecular weight olefins such as 1-decene and olefinic ethers and esters such as oleyl oleate. Polymeric olefins include polydecenes such as decene trimer, tetramer and/or pentamer and/or polyoctenes such as octene tetramer, pentamer, hexamer and/or heptamer.

The vicinal diols can be synthesized using several methods known to the art. One such method, described in *J. Am. Chem. Soc.*, 68, 1504 (1946), involves the hydroxylation of 1-olefins with peracids. Vicinal diols can also be prepared by the peroxytrifluoroacetic acid method for the hydroxylation of olefins as described in *J. Am. Chem. Soc.*, 76, 3472 (1954). Similar procedures can be found in U.S. Pat No. 2,411,762, U.S. Pat. No. 2,457,329 and U.S. Pat. No. 2,455,892. These are incorporated herein by reference.

The diols can also be prepared via catalytic epoxidation of an appropriate olefin, followed by hydrolysis.

Although, any suitable diol, can be used, preferred are vicinal diols which contain 10 to 30 carbon atoms. This range is preferred because diols having much less than 10 or 12 carbon atoms have significantly less friction reducing properties, while in those having more than 20 carbon atoms, solubility constraints become significant. More preferred are the $C_{14}$ to $C_{18}$ hydrocarbyl groups and mixtures of such hydrocarbyl groups in which solubility, frictional characteristics and other properties appear to be maximized.

The reaction products of polymeric olefins e.g., polyisobutene or polydecene with various functionalized diol and/or diol-ester derived phosphites are illustrated in the examples as disclosed below:

Among the diols contemplated are 1,2-decanediol, 1,2-dodecanediol, 1,2-tetradecanediol, 1,2-pentadecanediol, 1,2-hexadecanediol, 1,2-heptadecanediol, 1,2-octadecanediol, etc. mixed 1,2-$C_{15}$-$C_{18}$ alkanediols, mixed 1,2-$C_{13}$-$C_{16}$ alkanediols, and mixtures of all such diols, including mixtures of similar diols.

Diol esters include glycerol monooleate, trimethylolpropane monooleate, pentaerythritoldioleate and the like. Also included are glycerol dioleate, trimethylolpropane dioleate, pentaerythritol trioleate and the like.

The reactants, olefins or polyolefins and phosphites, may be obtained commercially, or prepared in any manner known in the art.

The reaction products are generally made by reacting a $C_2$ to about $C_{12}$ polyolefin, e.g., polyisobutene or polydecene with a mixture of a diol phosphites containing from 2 to about 22 carbon atoms in molar ratios of 2 to 1 of polyolefin to mixed diol phosphite. However, the molar ratio may vary from about 1 to 3 to about 3 to 1. The reaction parameters are not believed to be critical, they vary widely depending on the particular reactants and the desired products.

It is emphasized here that these materials may be used as base oils or lubricating fluids (basestock) or as an additive product. When used as a base oil, the base should contain alkyl moieties having from at least about 20 to about 36 carbon atoms or as many as 200 carbon atoms with a molecular weight range of 300 to 3000 with 500 to 1500 being preferred. Temperature of reaction is not believed to be critical, however, it will depend upon specific reactants as well as the solvent, if one is used. The reaction may take place at temperatures varying from about 80° to about 225° C. from about 3 to about 12 hours and autogenous pressure, or slightly higher pressures may be used if desired. Also a solvent may be used if desired, any known hydrocarbon solvent such as toluene, benzene, xylene, cyclohexane and the like are highly suitable. Diluent oil can also be used as a solvent.

The reactants are preferably used in appropriate molar quantities, that is, the reaction mixture should contain at least one mole each of the reactants, that is of polyolefin and diol or mixed diol phosphite, i.e. of olefin to diol or diol phosphite the molar ratio is preferred to be 1:1 to 1:3 or 3:1, preferably 1.5:1 to 2:1. Generally speaking the molar ratio of olefin to phosphite varies from 6:1 to about 1:6. However, up to a 5 or 10 fold excess or deficiency of any reactant can be used.

The additives may be incorporated into any suitable liquid fuel or lubricating media which comprises oils of lubricating viscosity, e.g., mineral or synthetic; or mixtures of mineral and synthetic or greases in which the aforementioned oils are employed as a vehicle or into such functional fluids as hydraulic fluids, brake fluids, power transmission fluids and the like. In general, mineral oils and/or synthetic, employed as the lubricant oil, or grease vehicle may be of any suitable lubricating viscosity range, as for example, from about 45 SSU at 100° F. to about 6000 SSU at 100° F., and, preferably, from about 50 to about 250 SSU at 210° F. These oils may have viscosity indices from below zero to about 100 or higher. Viscosity indices from about 70 to about 95 are preferred. The average molecular weight of these oils may range from about 250 to about 800. Where the lubricant is to be employed in the form of a grease, the lubricating oil is generally employed in an amount sufficient to balance the total grease composition, after accounting for the desired quantity of the thickening agent and other additive components to be included in the grease formulation.

In instances where synthetic oil, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxyphenyl) ether, phenoxy phenylethers, etc.

Fully formulated lubricating oils may include a variety of supplemental additives (for their known purpose) such as dispersants, detergents, inhibitors, antiwear agents, antioxidants, antifoam agents, pour depressants, antistaining agents and other additives including phenates, sulfonates and zinc dithiophosphates. As hereinbefore indicated, the aforementioned additive compounds may be incorporated as multifunctional agents in grease compositions. When high temperature stability is not a requirement of the finished grease, mineral oils having a viscosity of at least 40 SSU at 150° F., and particularly those falling within the range from about 60 SSU to about 6,000 SSU at 100° F. may be employed. The lubricating vehicles of the improved greases of the present invention, containing the above described additives, are combined with a grease forming quantity of a thickening agent. For this purpose, a wide variety of materials dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickeners may be employed which do not melt and dissolve when used at the required temperature within a particular environment; soap thickeners such as metallic (lithium or calcium) soaps including hydroxy stearate and/or stearate soaps can be used however, in all other respects, any material which is normally employed for thickening or gelling hydrocarbon fluids or forming greases can be used in preparing the aforementioned improved greases in accordance with the present invention.

Included among the preferred thickening agents are those containing at least a portion of alkali metal, alkaline earth metal or amine soaps of hydroxyl-containing fatty acids, fatty glycerides and fatty esters having from 12 to about 30 carbon atoms per molecule. The metals are typified by sodium, lithium, calcium and barium. Preferred is lithium. Preferred members among these acids and fatty materials are 12-hydroxystearic acid and glycerides containing 12-hydroxystearates, 14-hydroxystearic acid, 16-hydroxystearic acid and 6-hydroxystearic acid.

Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and and soaps of low-, intermediate and high-molecular weight acids and of nut oil acids.

The liquid fuels contemplated include the liquid hydrocarbons such as gasoline, fuel oil and diesel oil and the liquid alcohols such as methanol and ethanol. The fuels also include mixtures of alcohols as well as mixtures of alcohols and liquid hydrocarbons such as gasohol.

As has been disclosed hereinabove, the reaction products are useful as multifunctional antiwear/antioxidant/antirust agents. They are added to the lubricating medium in amounts sufficient to impart such properties to the lubricant. More particularly, such properties will be imparted to the lubricant by adding from about 0.01% to about 10% by weight, preferably from about 0.01% to about 3%, of the neat product. The reaction products can also be used as the lubricant fluid itself in concentrations of from 10 to 90% or even up to 100%. This use is often preferred in that a functionalized lubricant's performance is enhanced. Generally the products of this invention are added to fuels in the amount of about 25 lbs to about 500 lbs per 1000 bbls of fuels, preferably 50 to 250 lbs.

The following exemplary material is illustrative only and is not intended in any way as a limitation on the embodied invention.

EXAMPLE 1

To a four-neck round bottom flask equipped with a mechanical stirrer, condenser, thermometer, and nitrogen purge was added 92 grams (0.20 mol) of polyisobutene and heated to 120° C., then 40 ml of toluene solution with 59 grams (0.10 mol) of a mixed 1,2-hexadecane diol and 1,2-octadecane diol phosphite, and 4.5 grams (3 wt %) of di-tert-butyl peroxide was added dropwise. At the end of addition, the reaction mixture was heated to reflux for four hours, before stripping off solvent under vacuum at 130° C., which resulted in 147 grams of yellow fluid, which solidified to a creamy wax.

EXAMPLE 2

Under the same reaction conditions as described in Example 1, a toluene solution of mixed diol derived phosphite (59 grams, 0.10 mol) and di-tert-butyl peroxide (2.6 grams, 3 wt %) was added in dropwise to 1-decene (28 grams, 0.20 mol). The final product was 77.5 grams of a creamy wax.

EXAMPLE 3

Under the same reaction conditions as described in Example 1, a 30 ml toluene solution of diol phosphite (30 grams, 0.05 mol) and di-tert-butyl peroxide (2.5 grams, 3.0 wt %) was added to oleyl oleate (53 grams, 0.10 mol). The reaction yielded 82 grams of a creamy wax.

The products of the above examples were evaluated as lubricant additives at 1.0 wt % concentration in mineral oil. The results were compared to the test oil without additive. These data were obtained on the Four-Ball Wear Apparatus (2000 rpm, 200° F., 60 kg).

FOUR-BALL TEST

In this test three stationary balls are placed in a lubricant cup and a lubricant containing the additive to be tested is added thereto. A fourth ball is placed on a chuck device which can be used to spin the ball at known speeds and loads. 1% by weight of each product was placed in a blend of solvent paraffinic bright and in solvent paraffinic neutral mineral oils. These were blended in the ratios of 80/20 respectively. The samples were tested as specified hereinabove at 2000 rpm, 200° F., 60 kg. The following Table summarizes the test data.

| FOUR-BALL WEAR TEST | | |
|---|---|---|
| 1.0 wt % additive in mineral based oil (80% solvent paraffinic bright, 20% solvent paraffinic neutral mineral oils) | Wear Scar (mm) | $K \times 10^8$ * K factor |
| 0% Additive | 3.51 | 4995 |
| Example 1 | 0.64 | 4.74 |
| Example 2 | 0.57 | 2.74 |
| Example 3 | 0.55 | 2.20 |

* Wear Factor
$$K_t = \frac{X}{PVT}$$
$K_t$ = Wear factor (based on thickness change) (express as whole number times 10)
$X$ = Thickness change, in (wear)
$P$ = Contact Pressure, psi
$V$ = Velocity, ft/min
$T$ = Test Duration, h The additives in accordance with the invention were also evaluated according to the "Hot Tube Test." The result of the "Hot Tube Test" demonstrates that the coupling of the polyisobutylene and related olefins with the cyclic diol-and/or diol-ester derived phosphites described in this application provides novel lubricants and lubricant additives with enhanced multifunctional characteristics including thermal/oxidative stability, reduced wear, improved rust inhibition, load-carrying capabilities, and dispersancy.

The bench test used in our evaluation is an analytical method described below and entitled, "Hot Tube Oxidative/Thermal Stability Test for Marine and Automotive Engine Oils."

In brief, additives are blended into synthetic engine oil without dispersant, these blended oils were passed through an aluminum heating block via capillary pyrex tube, with a flow rate of 0.35 ml/hour and 10.0 cc/min. of air feed rate, the temperature of aluminum block was maintained at 295° C. for a total of 16 hours. These capillary pyrex tubes were only flushed with hexenes to remove oil but not lacquer and carbon deposits, and rated for lacquer and carbon deposits.

A rating scale from 1 to 9 is used, with 1 being clean and 9 being worst with black carbon deposit. (Reference standards are used for rating tubes.)

Hot Tube Test

-continued

| 295° C., 0.35 ml/hr flow rate, 10 ml/min air rate | |
|---|---|
| Item | Rating |
| Synthetic engine oil formulation with metallic detergent and inhibitor, but without dispersant as reference oil | 9 |
| 2% of Example 1 in above oil | 7 |
| 2% of Example 3 in above oil | 6 |

| Catalytic Oxidation Test 325° F., 40 hours | | |
|---|---|---|
| Item | Change in Acid Number ΔTAN | % Change in Kinematic Viscosity ΔKV % |
| Base oil (100% solvent paraffinic neutral mineral oil) | 6.85 | 78.1 |
| 1% of Example 1 in above oil | 2.62 | 43.0 |
| 1% of Example 3 in above oil | 4.80 | 56.2 |

The mixed 1,2-hexadecane diol and 1,2-octadecane diol phosphite is not soluble in synthetic engine oil.

The additive products described herein are highly effective for their intended purpose in both lubricants and liquid hydrocarbon fuels in the minor additive amounts disclosed hereinabove.

Although the present invention has been described with preferred embodiments, it is to be understood that modifications and variations may be resorted to, without departing from the spirit and scope of this invention, as those skilled in the art will readily understand. Such modifications and variations are considered to be within the scope of the appended claims.

What is claimed is:

1. An improved lubricant composition comprising a major proportion of an oil of lubricating viscosity or a grease prepared therefrom and a minor multifunctional antiwear, antioxidant, extreme pressure amount of olefin-phosphate adduct reaction products of (a) olefins or oligomers thereof having at least one free olefinic group and (b) aliphatic diol-derived phosphites having the following generalized structure:

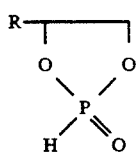

where R is an alkyl group of 1 to 12 carbon atoms, phenyl, or aralkyl and R optionally contains oxygen, sulfur or nitrogen or mixtures thereof.

2. The composition of claim 1 wherein said oil of lubricating viscosity is selected from (1) mineral oils, (2) synthetic oils, (3) a mixture of mineral and synthetic oils, (4) or is a grease prepared from any one of (1), (2), or (3).

3. The composition of claim 2 wherein said oil is mineral oil.

4. The composition of claim 2 wherein said oil is synthetic oil.

5. The composition of claim 2 wherein said oil is a mixture of mineral and synthetic oils.

6. The composition of claim 2 wherein said composition is a grease prepared from said oil of lubricating viscosity.

7. The composition of claim 1 having from about 0.001 to about 10 wt% based on the total weight of the composition of said olefin-phosphite adduct.

8. An improved lubricant composition having multifunctional antioxidant/antiwear/extreme pressure characteristics comprising from about 0 to about 50 wt.% of an oil of lubricating viscosity or a grease prepared therefrom and from about 50 to about 100 wt% of a product of reaction between (a) olefins selected from the group consisting of $C_2$ to about $C_{80}$ hydrocarbyl alpha and internal olefins, or oligomers thereof having at least one free olefinic group and (b) aliphatic diol-derived phosphites having the following generalized structure:

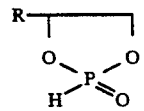

where R is an alkyl group of 1 to 12 carbon atoms, phenyl, or aralkyl and R optionally contains oxygen, sulfur or nitrogen or mixtures thereof.

9. The composition of claim 8 having from about 60 to about 90 wt% of said olefin-phosphite product of reaction.

10. A product of reaction made by reacting (a) $C_2$ to about $C_{80}$ hydrocarbyl alpha or internal olefin having at least one free olefinic group and (b) diol-derived phosphite having the following generalized structure:

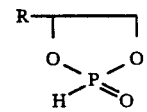

where R is an alkyl group of 1 to 12 carbon atoms, phenyl, or aralkyl and R optionally contains oxygen, sulfur or nitrogen or mixtures thereof and wherein (a) and (b) are reacted in a molar ratio of olefin to phosphite of from about 6:1 to about 1:6 at reaction temperatures varying from about 80° to about 225° C.

11. The product of claim 10 wherein said olefin is selected from propylene, butene, hexene, octene, decene, dodecene, isobutene and 1-decene.

12. The product of claim 10 wherein said olefin is an oligomeric olefin and wherein the oligomer consists of olefin monomers selected from the group consisting of propylene, butene, isobutene, hexene, heptene, octene, decene, and 1-decene, or mixtures thereof.

13. The product of claim 10 wherein said reaction takes place in the presence of a solvent.

14. The product of claim 13 wherein said solvent is selected from the group consisting of toluene, benzene and xylene.

15. The product of claim 14 wherein said solvent is toluene.

16. An improved lubricant composition comprising a major proportion of an oil of lubricating viscosity or a grease prepared therefrom and a minor multifunctional antiwear, antioxidant, extreme pressure amount of olefin-phosphite adduct reaction products of (a) olefins or oligomers thereof having at least one free olefinic group and (9) a mixture of diol-derived phosphites wherein said olefin-phosphite adduct is derived from the reaction of a $C_2$ to about $C_{60}$ olefin reactant, and said mixture of diol-derived phosphites are derived from a mixture of $C_4$ to about $C_{20}$ diols.

17. The composition of claim 16 wherein said olefin is isobutene, and said mixture of diol-derived phosphites are 1,2-hexadecane diol phosphite and 1,2-octadecane diol phosphite.

18. The composition of claim 16 wherein said olefin is 1-decene, and said mixture of diol-derived phosphites are 1,2-hexadecane diol phosphite and 1,2-octadecane diol phosphite.

19. A product of reaction made by reacting (a) $C_2$ to about $C_{80}$ hydrocarbyl alpha or internal olefin having at least one free olefinic group and (b) a mixture of 1,2-hexadecane diol phosphite and 1,2-octadecane diol phosphite wherein (a) and (b) are reacted in a molar ratio of olefin to phosphite of from about 6:1 to about 1:6 at reaction temperatures varying from about 80° to about 225° C.

* * * * *

UNITED STATES PATENT AND TRADEMARK OFFICE
CERTIFICATE OF CORRECTION

PATENT NO. : 5,254,276

DATED : October 19, 1993

INVENTOR(S) : L.A. Benjamin et al.

It is certified that error appears in the above-identified patent and that said Letters Patent is hereby corrected as shown below:

Column 9, Line 39, Delete "phosphate" and insert --phosphite--

Signed and Sealed this

Seventh Day of June, 1994

*Attest:*

BRUCE LEHMAN

*Attesting Officer*     *Commissioner of Patents and Trademarks*